United States Patent
Vitali et al.

(10) Patent No.: US 7,662,103 B2
(45) Date of Patent: Feb. 16, 2010

(54) APPARATUS FOR NON-INVASIVE DIAGNOSIS OF VASOVAGAL SYNCOPE IN A PATIENT

(75) Inventors: Luca Vitali, Strambino (IT); Guido Gaggini, Milan (IT)

(73) Assignee: Ela Medical S.A.S., Montrouge (FR)

( * ) Notice: Subject to any disclaimer, the term of this patent is extended or adjusted under 35 U.S.C. 154(b) by 597 days.

(21) Appl. No.: 11/316,333

(22) Filed: Dec. 21, 2005

(65) Prior Publication Data

US 2006/0189874 A1    Aug. 24, 2006

(30) Foreign Application Priority Data

Dec. 21, 2004   (FR)   .................................. 04 13646

(51) Int. Cl.
*A61N 1/00* (2006.01)
(52) U.S. Cl. ...................................................... 600/508
(58) Field of Classification Search ................. 600/585, 600/527, 508–509, 513; 607/17–19, 9, 23, 607/44
See application file for complete search history.

(56) References Cited

U.S. PATENT DOCUMENTS

| | | | |
|---|---|---|---|
| 5,496,351 A * | 3/1996 | Plicchi et al. .................. 607/17 |
| 5,957,957 A | 9/1999 | Sheldon | |
| 6,044,297 A | 3/2000 | Sheldon et al. | |
| 6,719,701 B2 * | 4/2004 | Lade ........................... 600/485 |
| 6,788,970 B1 * | 9/2004 | Park et al. ..................... 607/17 |
| 6,792,308 B2 * | 9/2004 | Corbucci ....................... 607/17 |
| 7,181,268 B2 * | 2/2007 | Sheldon et al. .............. 600/513 |
| 7,409,241 B2 * | 8/2008 | Vitali et al. .................. 600/513 |
| 2003/0040776 A1 | 2/2003 | Kroll et al. | |

* cited by examiner

*Primary Examiner*—George Manuel
*Assistant Examiner*—Robert N Wieland
(74) *Attorney, Agent, or Firm*—Orrick Herrington & Sutcliffe, LLP

(57) ABSTRACT

An apparatus for non-invasive diagnosis of states of vasovagal syncope in a patient placed on a tilt table and subjected to a tilt-test, the apparatus comprising: circuits for sensing the patient's endocardiac acceleration; circuits for sensing the patient's heart rate; and analyzer circuits receiving as inputs said endocardiac acceleration and said heart rate, and outputting information about the sympthetico-vagal activity of the patient. The circuits for sensing endocardiac acceleration comprise an external accelerator sensor suitable for being held in contact with the patient's rib cage. The analyzer circuits comprise classifier circuits suitable, in the event of a syncope occurring, for determining one type of syncope amongst a plurality of syncope types as a function of the endocardiac acceleration and heart rate values sensed during a plurality of heart cycles preceding the occurrence of the syncope.

11 Claims, 1 Drawing Sheet

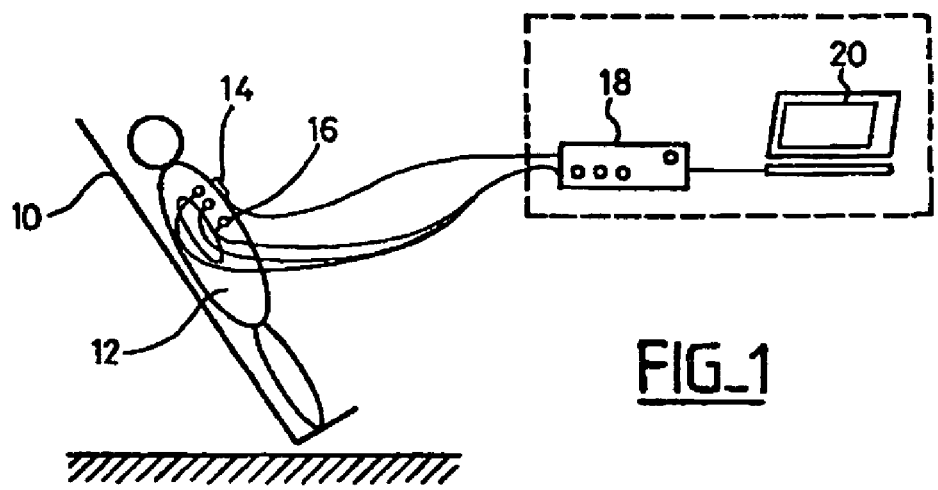
FIG_1
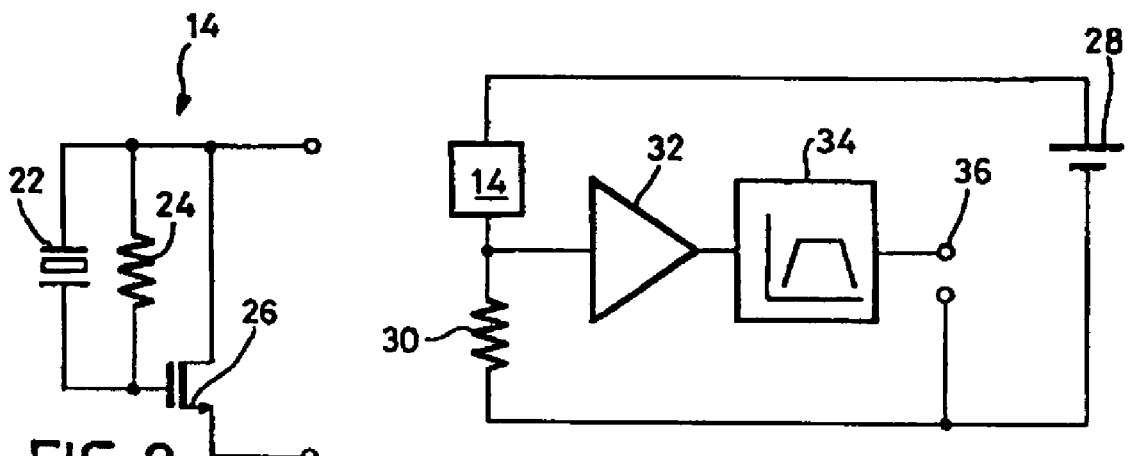
FIG_2  FIG_3
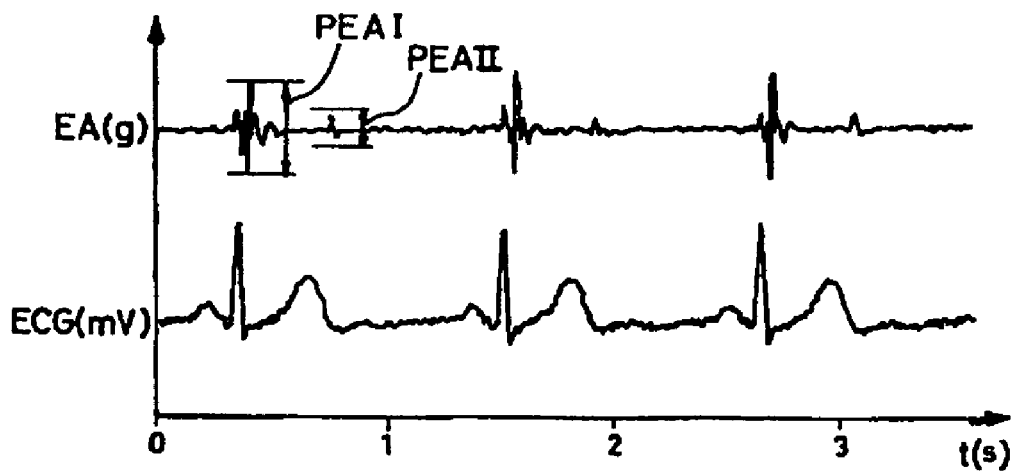
FIG_4

APPARATUS FOR NON-INVASIVE DIAGNOSIS OF VASOVAGAL SYNCOPE IN A PATIENT

FIELD OF THE INVENTION

The present invention relates to non-invasive diagnosis of states of vasovagal syncope in a patient

BACKGROUND OF THE INVENTION

Essentially, syncope is a temporary loss of consciousness with a drop in muscle tone, resulting from a momentary reduction in blood circulation in the brain. Amongst the various types of syncope, vasovagal syncope is that which is produced by a temporary imbalance in the system for regulating vasovagal equilibrium, leading to the vagal system being activated excessively, giving rise to vasodilation and bradycardia, causing syncope.

It is generally considered that vasovagal syncope comes from a state in which the sympathetic system presents particularly high reactivity having the effect of triggering and opposing an excessive response of the parasympathetic system, leading to vasodilation, itself inducing a reduction in the filling of the ventricles and bradycardia.

The complexity of these mechanisms makes determining the etiology of vasovagal syncope awkward, and consequently makes it difficult to prescribe any appropriate pharmacological or other therapy.

Until now, only complex and invasive methods have been available for studying the behavior of the autonomic nervous system of a subject, which is thus of limited application and generally restricted to a few special cases.

Thus, Mangin et al., in "Simultaneous Analysis Of Heart Rate Variability and Myocardial Contractility During Head-up Tilt In Patients With Vasovagal Syncope," published in the Journal of Cardiovascular Electrophysiology, Vol. 12, Issue 6, 639-644 (June 2001), have proposed using an endocardiac acceleration signal delivered by an implanted prosthesis to analyze the sympathico-vagal activity of a patient.

As described, for example, in EP-A-0 515 319 (assigned to Sorin Biomedica Cardio SpA), there exist pacemakers associated with an endocavity lead in which the distal electrode implanted at the end of the ventricle includes a micro-accelerometer suitable for measuring endocardiac acceleration. EP-A-0 655 260 (assigned to Sorin Biomedica Cardio SpA) describes one way of treating the endocavity acceleration signal delivered by that sensor situated at the end of the lead in order to detect certain cardiac disturbances and possibly trigger defibrillation therapy.

The above-identified article by Mangin et al. describes the result of clinical studies performed on a series of patients fitted with such prostheses, where attempts were made to provoke a syncope in such patients by means of a tilt-test, a test which itself is well known, having the purpose of revealing the origin of syncope that can be caused when a patient installed on a tilting table goes from a prone position to a highly inclined position, the result being considered positive if functional symptoms of syncope appear within a given length of time, including severe hypotension possibly associated with paradoxyl bradycardia.

The study reported in that article reveals a correlation between the levels of the peaks of endocardiac acceleration (PEA) and the propensity to develop syncope. Nevertheless, that study recognizes the limitation due to the small number of patients, who are necessarily patients who have received pacemakers specially provided with means for measuring endocardiac acceleration. In addition, the article draws no conclusions, whether therapeutically or diagnostically, from the correlation found between the variations in PEA and the occurrence of vasovagal syncope.

OBJECTS AND SUMMARY OF THE INVENTION

One of the objects of the present invention is to make equipment available to practitioners for diagnosing states of vasovagal syncope that is firstly non-invasive (and can thus be applied to any patient whether or not that patient is fitted with a pacemaker), and secondly delivers not only raw data to the practitioner (e.g., variations in PEA, heart rate), but also provides assistance in diagnosis, in particular concerning the type of syncope developed by the patient.

The apparatus of the invention is of the general type described in the aforementioned article by Mangin et al., i.e., comprising means for sensing the patient's endocardiac acceleration; means for sensing the patient's heart rate; and analyzer means receiving as inputs said endocardiac acceleration and said heart rate, and outputting information about the sympthetico-vagal activity of the patient.

In one embodiment of the invention, the means for sensing endocardiac acceleration comprise an external accelerator sensor suitable for being held in contact with the patient's rib cage; and the analyzer means comprise classifier means suitable, in the event of a syncope occurring, for determining one type of syncope amongst a plurality of types as a function of the endocardiac acceleration and heart rate values sensed during a plurality of heart cycles preceding occurrence of the syncope.

Most advantageously, the analyzer means determine at least one value as a function of one and/or the other of two endocardiac acceleration peaks during a given cycle, these peaks comprising a first peak during the constant volume ventricular contraction stage and a second peak during the constant volume ventricular relaxation stage. The classifier means then determine the type of syncope as a function of the values of the endocardiac acceleration peak(s) and of the heart rate as sensed during a plurality of heart cycles preceding occurrence of the syncope.

The classifier means determine the type of syncope as a function of an average of the values of the endocardiac acceleration peak(s) sensed during a plurality of heart cycles preceding occurrence of the syncope.

More particularly, the analysis means determine the long-term and short-term averages of the values of the first and second endocardiac acceleration peaks and heart rate values, and the classifier means then determine the type of syncope as a function of the differences between these long-term and short-term averages picked up during a plurality of heart cycles preceding the occurrence of the syncope.

A first type of syncope can then be determined when the short-term average of the values of the first acceleration peaks is less than the long-term average of the values of the first acceleration peaks weighted by a first proportionality factor, and the short-term average of the heart rate values is greater than the long-term average of the heart rate values, weighted by a second proportionality factor.

A second type of syncope can then be determined when the short-term average of the values of the second acceleration peaks is less than the long-term average of the values of the second acceleration peaks weighted by a third proportionality factor, and the short-term average of the heart rate value is greater than the long-term average of the heart rate value weighted by a fourth proportionality factor.

A third type of syncope can then be determined when the short-term average of the values of the second acceleration peaks is less than the long-term average of the values of the second acceleration peaks weighted by a fifth proportionality factor, less than said third proportionality factor, and the short-term average of the heart rate values is greater than the long-term average of the heart rate values weighted by a sixth proportionality factor, less than said fourth proportionality factor.

BRIEF DESCRIPTION OF THE DRAWINGS

Further benefits, features, and advantages will become apparent to a person of ordinary skill in the art from the following description of a preferred embodiment of the present invention, given with reference to the accompanying drawings wherein:

FIG. 1 is a diagrammatic view of the apparatus of the present invention, connected to a patient installed on a tilt table;

FIG. 2 shows the internal structure of the accelerometer sensor used;

FIG. 3 is a diagram of the input and shaping circuits for the signal delivered by the sensor of FIG. 2; and FIG. 4 is a timing diagram showing the variations in endocavity acceleration together with the corresponding surface electrocardiogram (ECG) and electrogram during three successive heart cycles.

DETAILED DESCRIPTION OF THE INVENTION

In FIG. 1, reference 10 designates a tilt table having a patient 12 installed thereon to be subjected to a tilt-test, in accordance with a technique that is itself conventional in the field of diagnosing syncope.

In one embodiment of the invention, the patient is fitted with an external accelerometer sensor 14 placed in the region of the sternum and held pressed against the rib cage, e.g., by a patch of the kind used for holding ECG electrodes in place, possibly with an outer covering of adhesive bandage.

The patient is also fitted with electrodes 16 for picking up a surface ECG, the signals picked up by the sensor 14 and the electrodes 16 being applied to signal amplifier and processor equipment 18 that delivers signals, preferably digital information, to a processor and display member 20, such as a microcomputer serving to present and analyze in real time the signals delivered by the sensor 14 and the electrodes 16.

FIG. 2 shows in greater detail the structure of the accelerometer sensor 14 which comprises a piezoelectric sensor element 22 biased by a resistor 24 and associated with a preamplifier metal oxide on silicon (MOS) transistor 26.

As can be seen in FIG. 3, the sensor 14 is biased by a voltage source 28 in series with a resistor 30. The output signal from the sensor is amplified by an amplifier 32 and is then shaped by a bandpass filter 34 and delivered to an output 36 for subsequent digitizing and processing.

In FIG. 4, the top curve shows variations in endocardiac acceleration (EA) as measured by the sensor 14. The corresponding trace of a surface electrocardiogram (ECG) is also shown in this figure, for three consecutive heart cycles.

As can be seen, endocardiac acceleration passes through two successive peaks of amplitude that can be determined by appropriately processing the signal delivered by the acceleration sensor, as known in the art and as described in above-mentioned EP-A-0 655 260. The term "peak" is used to mean the maximum peak-to-peak value of the acceleration signal between two extrema, one positive and the other negative, corresponding to the differences PEA I and PEA II marked on the timing chart of FIG. 4.

More precisely, the first peak of endocardiac acceleration (PEA I) corresponds to closure of the mitral and tricuspid valves, at the beginning of the constant volume ventricular contraction stage (systole). The variations in this first peak are closely associated with the variations in pressure in the ventricle (the amplitude of the peak PEA I being, more precisely, correlated to the positive maximum in pressure variation dP/dt in the left ventricle) and can thus constitute a parameter representative of the contractility of the myocardium, itself associated with the activity level of the sympathetic system.

The second peak of endocardiac acceleration (PEA II) corresponds to closure of the aortic and pulmonary valves, at the moment of the constant volume ventricular relaxation stage. This second peak, which is produced by the sudden deceleration of the mass of blood moving in the aorta, constitutes a parameter representative of peripheral blood pressure at the beginning of diastole. It also constitutes a key parameter of the physiological process that leads to occurrence of vasovagal syncope.

Clinical studies have shown that during a tilt-test, the variations in PEA I, in PEA II, and in heart rate vary in application of characteristic schemes that are suitable for use in distinguishing between different types of instabilities of the autonomic nervous system, and thus for constituting a diagnostic aid and an aid in defining therapy and follow-up for each patient.

The tilt-test can be implemented using the conventional protocol known as the "Westminster protocol": initially the patient rests prone on the back on the horizontal table for 30 minutes, and then the table is raised to 60° with the patient remaining in this position for a maximum duration of 45 minutes, after which the table is returned to the horizontal. If a syncope occurs before the end of the period of inclination, the test is considered as being positive, otherwise it is considered as being negative (i.e., no syncope).

Endocardiac acceleration and heart rate are monitored throughout the duration of the test, and the apparatus determines in real time the values for the parameters PEA I, PEA II, and heart rate.

These values are read during successive cycles and they are analyzed in order to classify the vasovagal syncope. It should be observed that this analysis can be applied to the PEA I signal on its own, to the PEA II signal on its own, or to a combination of both signals PEA I and PEA II associated with heart rate.

It is possible to determine the absolute values presented by the parameters relative to thresholds cycle by cycle, or preferably to determine a value that is averaged over a predetermined number of cycles in order to avoid the influence of cycle-to-cycle variability (measurement dispersion) and the influence of insignificant short events.

In order to improve the specificity of the classification, and in particular to take account of differences in the base values of the PEA parameters from one individual to another, it can be advantageous to analyze the variations of these parameters instead of their absolute values.

One way of proceeding is to analyze the difference between a short-term average and a long-term average of the same parameter. If this parameter varies little, the difference will be small and the two values will end up coinciding. However, as soon as the parameter becomes unstable, the short-term average will follow variations in the parameter more quickly than the long-term average. The difference between the two averages is then no longer zero or almost zero, but takes on a positive value (when the parameter increases) or a negative value (when the parameter decreases), with the absolute value of the difference depending on the parameter being analyzed and on its rate of variation.

In order to perform classification, one or more thresholds are determined, and each of the parameters PEA I or PEA II (or a combination of the two parameters) is compared with a predetermined threshold. The result of the comparison can be combined in various ways with the result of similar comparisons performed on other parameters (including heart rate) in order to produce an output signal having two or more states, each state being associated with a particular type of syncope.

Further details regarding implementation of such a technique are given below.

It is also possible to use a "state machine" type process in which the results of the comparisons with the various thresholds are applied to a memory and state transition system that performs classification in application of a more complex scheme for variation.

Other types of analysis can also be implemented, for example, using correlation techniques, techniques for analyzing signal morphology, frequency analysis techniques, wavelet analysis techniques, etc.

Classification can also take account not only of the parameters PEA I and/or PEA II, and heart rate, but also of signals delivered by an activity sensor, a minute ventilation sensor, etc.

It also should be understood that methods of detecting the patient's heart rate other than by acquiring an EKG may be used, e.g., optical detection of pulsating blood flow as in an oximeter, acoustic detection of the heartbeat and the like.

EXAMPLE

There follows a description of an example of a classification algorithm based on combined analysis of the first acceleration peak (PEA I), of the second acceleration peak (PEA II), and of heart rate.

These three quantities are measured for each heart cycle and an algorithm calculates, for each of them, two moving averages, one for the long term and the other for the short term, these averages being updated regularly (on each cycle, every four cycles, every ten cycles, etc.).

The algorithm thus determines the following six quantities:

PEA1LT: long-term moving average (e.g. over 1000 cycles) of the parameter PEA I;

PEA1ST: short-term moving average (e.g. over 30 cycles) of the parameter PEA I;

PEA2LT: long-term moving average (e.g. over 1000 cycles) of the parameter PEA II;

PEA2ST: short-term moving average (e.g. over 30 cycles) of the parameter PEA II;

HRLT: long-term moving average (e.g. over 5000 cycles) of the heart rate;

HRST: short-term moving average (e.g. over 100 cycles) of the heart rate.

To classify a syncope, the algorithm evaluates the following three boolean quantities:

$$(\text{PEA1ST} < k_1 \text{PEA1LT}) \& (\text{HRST} > k_2 \text{HRLT}) \quad (1)$$

$$(\text{PEA2ST} < k_3 \text{PEA2LT}) \& (\text{HRST} > k_4 \text{HRLT}) \quad (2)$$

$$(\text{PEA2ST} < k_5 \text{PEA2LT}) \& (\text{HRST} > k_2 \text{HRLT}) \quad (3)$$

A numerical example for the factors k1 to k6 is as follows:

$$(\text{PEA1ST} < 0.75 \text{ PEA1LT}) \& (\text{HRST} > 1.15 \text{ HRLT}) \quad (1)$$

$$(\text{PEA2ST} < 0.95 \text{ PEA2LT}) \& (\text{HRST} > 1.15 \text{ HRLT}) \quad (2)$$

$$(\text{PEA2ST} < 0.55 \text{ PEA2LT}) \& (\text{HRST} > \text{HRLT}) \quad (3)$$

If condition (1) is true, that indicates that the heart rate has increased above its base value, and the parameter PEA I has decreased—i.e., that myocardiac contractility has decreased, indicating a drop in activity of the sympathetic system.

If condition (2) is true, that indicates that the heart rate has increased above its base value, and the parameter PEA II has decreased—i.e., that the peripheral diastolic blood pressure has decreased.

Condition (3) corresponds to condition (2), but involves the application of stricter criteria, and indicates that the autonomic nervous system is no longer capable of keeping blood pressure stable.

Each of these conditions is associated with a particular type of syncope:

type I syncope for condition (1), i.e., a reduction in PEA I preceding the occurrence of the syncope, associated with a heart rate situated above the base level: when this type of syncope is observed it indicates clearly that the autonomic nervous system has an influence on the appearance of the symptoms;

type II syncope for condition (2), in which the decrease in PEA II associated with a heart rate situated above the base level reveals on the contrary probable vaso-depressive etiology; and type III syncope for condition (3), with a rapid decline in PEA II that is correlated little or not at all with an increase in heart rate, reveals the dominant influence of the autonomic nervous system on the appearance of the syncope.

As can be seen from the above, implementing the apparatus of the invention is particularly simple and non-invasive, insofar as it involves only applying the accelerometer sensor to the patient's rib cage and acquiring the heart rate.

Furthermore, using this apparatus does not lengthen the duration of diagnosis, since it is performed during the inclination test session, which would have been performed in any event.

In this novel manner, the apparatus of the invention analyzes the behavior of the autonomic nervous system during the period preceding vasovagal syncope, an approach which has not been investigated in the past, since it was believed that it would require procedures that are complex and lengthy to implement, or else that it was limited to certain types of patient already fitted with a suitable implanted device (as in the above-mentioned article by Mangin et al.).

Various implementations can be envisaged as variations or as additions of the method of classification given above by way of example.

In particular, it is possible to classify syncope on the basis of analyzing the energy contained in the endocardiac acceleration signal at the PEA I peak and/or the PEA II peak, or indeed to classify syncope on the basis of analyzing the same endocardiac acceleration signal, such as performing time/frequency analysis or analyzing the area under the curve of the signal, or indeed analyzing the width of the peak.

One skilled in the art will appreciate that the present invention can be practiced by other than the described embodiments, which are presented for purposes of illustration and not of limitation.

We claim:

1. An apparatus for non-invasive diagnosis of states of vasovagal syncope in a patient placed on a tilt table and subjected to a tilt-test, the apparatus comprising:

means for sensing the patient's endocardiac acceleration;
means for sensing the patient's heart rate; and
analyzer means receiving as inputs said endocardiac acceleration and said heart rate, and outputting information about the sympathetico-vagal activity of the patient; wherein:
the means for sensing endocardiac acceleration comprise an external accelerator sensor suitable for being held in contact with the patient's rib cage; and
the analyzer means comprise classifier means suitable, in the event of a syncope occurring, for determining one type of syncope amongst a plurality of syncope types as a function of the endocardiac acceleration and heart rate values sensed during a plurality of heart cycles preceding the occurrence of the syncope.

2. The apparatus of claim 1, wherein:
the analyzer means are means suitable for determining at least one value as a function of one of a plurality of endocardiac acceleration peaks during a given cycle, these peaks comprising a first peak during the constant volume ventricular contraction stage and a second peak during the constant volume ventricular relaxation stage; and
the classifier means are means suitable for determining the type of syncope as a function of the values of the endocardiac acceleration peaks and of the heart rate as sensed during a plurality of heart cycles preceding the occurrence of the syncope.

3. The apparatus of claim 2, wherein the classifier means are means suitable for determining the type of syncope as a function of an average of the values of the endocardiac acceleration peaks sensed during a plurality of heart cycles preceding the occurrence of the syncope.

4. The apparatus of claim 2, wherein the classifier means are means suitable for determining the type of syncope as a function of the variation in the values of the endocardiac acceleration peaks sensed during a plurality of heart cycles preceding the occurrence of the syncope.

5. The apparatus of claim 2, wherein the analyzer means comprise means for determining:
a long-term average and a short-term average of the values of the first endocardiac acceleration peaks sensed during the constant volume ventricular contraction stage during a plurality of successive cycles; and/or
a long-term average and a short-term average of the values of the second endocardiac acceleration peaks sensed during the constant volume ventricular relaxation stage during a plurality of successive cycles; and
a long-term average and a short-term average of the heart rate values;
and in which the classifier means are means suitable for determining the type of syncope as a function of differences between the long-term and short-term averages of the values of the endocardiac acceleration peak(s) sensed during a plurality of heart cycles preceding the occurrence of the syncope.

6. The apparatus of claim 5, wherein the classifier means are means suitable for determining a type of syncope when:
the short-term average of the values of the first acceleration peaks is less than the long-term average of the values of the first acceleration peaks weighted by a first proportionality factor; and
the short-term average of the heart rate values is greater than the long-term average of the heart rate values weighted by a second proportionality factor.

7. The apparatus of claim 6, wherein the classifier means are means suitable for determining a type of syncope when:
the short-term average of the values of the second acceleration peaks is less than the long-term average of the values of the first acceleration peaks weighted by a third proportionality factor; and
the short-term average of the heart rate values is greater than the long-term average of the heart rate values weighted by a fourth proportionality factor.

8. The apparatus of claim 7, wherein the classifier means are means suitable for determining a type of syncope when:
the short-term average of the values of the second acceleration peaks is less than the long-term average of the values of the first acceleration peaks weighted by a fifth proportionality factor, less than said third proportionality factor; and
the short-term average of the heart rate values is greater than the long-term average of the heart rate values weighted by a sixth proportionality factor, less than said fourth proportionality factor.

9. The apparatus of claim 5, wherein the classifier means are means suitable for determining a type of syncope when:
the short-term average of the values of the second acceleration peaks is less than the long-term average of the values of the first acceleration peaks weighted by a third proportionality factor; and
the short-term average of the heart rate values is greater than the long-term average of the heart rate values weighted by a fourth proportionality factor.

10. The apparatus of claim 5, wherein the classifier means are means suitable for
determining a type of syncope when:
the short-term average of the values of the second acceleration peaks is less than the long-term average of the values of the first acceleration peaks weighted by a fifth proportionality factor, less than said third proportionality factor; and
the short-term average of the heart rate values is greater than the long-term average of the heart rate values weighted by a sixth proportionality factor, less than said fourth proportionality factor.

11. An apparatus for non-invasive diagnosis of states of vasovagal syncope in a patient placed on a tilt table and subjected to a tilt-test, the apparatus comprising:
an external accelerator sensor having an output corresponding to endocardiac acceleration;
a plurality of electrodes operative to detect a cardiac activity; and
a microcomputer responsive to said detected cardiac activity and endocardiac acceleration, wherein said microcomputer comprises an algorithm for classifying, in the event of a syncope occurring, one type of syncope amongst a plurality of syncope types as a function of said detected endocardiac acceleration and heart rate values sensed in said detected cardiac activity during a plurality of heart cycles preceding the occurrence of the syncope.

* * * * *